(12) United States Patent
Kuklinski et al.

(10) Patent No.: US 10,231,994 B2
(45) Date of Patent: Mar. 19, 2019

(54) SELENIUM-CONTAINING COMPOSITIONS AND USES THEREOF

(71) Applicant: SELO MEDICAL GMBH, Unternberg (AT)

(72) Inventors: Bodo Kuklinski, Rostock (DE); Peter Kössler, Mariapfarr (AT); Norbert Fuchs, Mariapfarr (AT)

(73) Assignee: SELO MEDICAL GMBH, Unternberg (AT)

( * ) Notice: Subject to any disclaimer, the term of this patent is extended or adjusted under 35 U.S.C. 154(b) by 0 days.

(21) Appl. No.: 15/725,455

(22) Filed: Oct. 5, 2017

(65) Prior Publication Data

US 2018/0028559 A1 Feb. 1, 2018

Related U.S. Application Data

(62) Division of application No. 12/913,585, filed on Oct. 27, 2010, now Pat. No. 9,801,904, which is a division of application No. 10/497,504, filed as application No. PCT/AT02/00336 on Dec. 4, 2002, now Pat. No. 7,850,996.

(30) Foreign Application Priority Data

Dec. 4, 2001 (AT) .................................. A 1895/2001

(51) Int. Cl.
| | |
|---|---|
| *A61K 31/19* | (2006.01) |
| *A61K 33/00* | (2006.01) |
| *A61K 33/04* | (2006.01) |
| *A61K 31/194* | (2006.01) |

(52) U.S. Cl.
CPC .............. *A61K 33/04* (2013.01); *A61K 31/19* (2013.01); *A61K 31/194* (2013.01); *A61K 33/00* (2013.01); *Y10S 514/90* (2013.01); *Y10S 514/901* (2013.01); *Y10S 514/902* (2013.01)

(58) Field of Classification Search
CPC ...... A61K 33/04; A61K 33/00; A61K 31/194; A61K 31/19
See application file for complete search history.

(56) References Cited

U.S. PATENT DOCUMENTS

| 4,512,977 | A | | 4/1985 | Lundy |
| 4,529,587 | A | * | 7/1985 | Green ...................... A61K 8/67 424/47 |
| 4,668,515 | A | | 5/1987 | Bankit et al. |
| 4,681,753 | A | | 7/1987 | Revici |
| 4,762,726 | A | | 8/1988 | Soucie et al. |
| 4,865,840 | A | * | 9/1989 | Burke ...................... A61K 8/19 424/59 |
| 5,153,230 | A | | 10/1992 | Jaffery |
| 5,182,104 | A | | 1/1993 | Marcus et al. |
| 5,425,944 | A | | 6/1995 | Harich |
| 5,470,880 | A | | 11/1995 | Yu et al. |
| 5,512,200 | A | | 4/1996 | Garcia |
| 5,536,497 | A | | 7/1996 | Evans et al. |
| 6,069,152 | A | | 5/2000 | Schaus et al. |
| 6,114,348 | A | | 9/2000 | Weber et al. |
| 6,120,758 | A | | 9/2000 | Siddiqui et al. |
| 6,133,237 | A | | 10/2000 | Noll et al. |
| 6,277,835 | B1 | | 8/2001 | Brown |
| 6,391,323 | B1 | | 5/2002 | Carnevali |
| 2003/0180387 | A1 | | 9/2003 | Kossler et al. |
| 2004/0265268 | A1 | * | 12/2004 | Jain .......................... A61K 8/64 424/85.1 |
| 2005/0048134 | A1 | | 3/2005 | Kuklinski et al. |

FOREIGN PATENT DOCUMENTS

| DE | 3408362 | 9/1984 |
| DE | 43 20 694 | 1/1995 |
| DE | 43 35 441 | 4/1995 |
| DE | 44 13 839 | 10/1995 |
| EP | 0 000 670 | 2/1979 |
| EP | 0 750 911 | 1/1997 |
| EP | 0 913 155 | 5/1999 |
| FR | 2 779 720 | 12/1999 |
| GB | 2323030 | 9/1998 |
| WO | WO 00/12101 | 3/2000 |
| WO | WO 00/28977 | 5/2000 |
| WO | WO 01/93910 | 12/2001 |
| WO | WO 02/072112 | 9/2002 |
| WO | WO 03/047604 | 6/2003 |

OTHER PUBLICATIONS

"Bromelains," Reynolds JEF (Editor). Martindale: The Extra Pharmacopeia (Twenty-Eight Edition). The Pharmaceutical Press, London, pp. 646, 1982.
"Hydroxy Acid," Stedman's Medical Dictionary (Twenty-Second Edition). Williams and Wilkins Company, pp. 595, 1972.
"Melanoma," The Merck Manual-Second Home Edition [Online] 1995-2000.
"Preventive" and "Prophylactic," Stedman's Medical Dictionary (Twenty-Second Edition). Williams and Wilkins Company, pp. 1017, 1025, 1972.
"Vitamin C," Stedman's Medical Dictionary (Twenty Fifth Edition). Williams and Wilkins, pp. 1725-1726, 1990.
Carey, "Carbonic Acid," Organic Chemistry (Fourth Edition). McGraw Hill, pp. 749, 2000.
Crowley, "Solutions, Emulsions, Suspensions, and Extracts," Chapter 39. Remington: The Science and Practice of Pharmacy, 21$^{st}$ Edition, 2005, pp. 745-775.
DE 43 20 694 A1 USPTO translation.
Eisenberg et al., "Interactions of Selenium and Fluoride on Growth, Glycolysis and Survival of *Streptococcus mutans* GS-5," *Caries Research*, 24: 306-311, 1990.

(Continued)

*Primary Examiner* — John Pak
*Assistant Examiner* — Nathan W Schlientz
(74) *Attorney, Agent, or Firm* — Norton Rose Fulbright US LLP

(57) ABSTRACT

The use of selenite- or selenate-containing preparations supplemented with pharmaceutically acceptable or food-compatible acids for the preparation of an agent intended for topical or buccal application or mucosal administration is described.

9 Claims, No Drawings

(56) References Cited

OTHER PUBLICATIONS

Emmert, "Treatment of Common Cutaneous Herpes Simplex Virus Infections," *American Family Physician*, 61:1697-1706, 1708, 2000.

English et al., "Dermatoses of the of glans penis and prepuce," *Journal of the American Academy of Dermatology*, 37(1): 1-24, 1997 (Abstract).

Fu et al., "Proteomic study on sodium selenite-induced apoptosis of human cervical cancer HeLa cells", *Journal of Trace Elements in Medicine and Biology*, 25(3):130-137, 2011.

Ganther and Kraus, containing ascorbic "Chemical stability of selenious acid in total parenteral nutrition solutions acid," *J. of Parenteral and Enteral Nutrition*, 13:185-188, 1989.

Ganther, "Metabolism of hydrogen selenide and methylated selenides," Advances in Nutrional Research, Draper HH, editor, New York-Plenum Press, 2:107-128, 1979.

Gonzalez, "Ascorbic Acid and Selenium Interaction: Its Relevance in Carcinogenesis," *Journal of Orthomolecular Medicine*, 5(2): 67-69, 1990.

Haas et al., "The Pathogenesis of Hemorrhoids," *Dis Colon Rectum*, 27:442-50, 1984.

Hong et al., "Detection of Level of Selenium in Cervical Tissues of Patients with Human Papillomavirus Infection," Zhongguo Redai Yixue, 2008, 8(8), pp. 1315-1316 (English Abstract).

Hussain et al., "Chemopreventive Action of Selenium on Methylcholanthrene-Induced Carcinogenesis in the Uterine Cervix of Mouse" *Oncology*, 49: 237-240, 1992.

International Preliminary Report on Patentability issued in PCT Application No. PCT/AT2012/00032, dated Aug. 21, 2013.

International Search Report issued in PCT Application No. PCT/AT2012/00032, dated Apr. 4, 2012.

Introduction to modern pharmaceuticals ($3^{rd}$ edition), Apr. 10, 1987, p. 414-416 (published in Japanese).

Ismail et al., "Prevention of periodontal disease," *Canadian Task Force on the Periodic Health Examination, Canadian Guide to Clinical Preventive Health Care*, Ottawa: Health Canada, 420-431, 1994.

Liang et al., "Sodium Selenite Induced HeLa cells Apoptosis", *Nat Sci Ed*, 51(6): 663-667, 2005. (Chinese)—[English Abstract provided].

Lutsoia et al., "Correlation of the Nitrate and Ascorbic Acid Content in Vegetables and Fruit," *Vopr. Pitan.*, 3:54-57, 1980 (Abstract).

Manola et al., "Prognostic Factors in Metastatic Melanoma: A Pooled Analysis of Eastern Cooperative Oncology Group Trials," *Journal of Clinical Oncology*, 18:3782-3793, 2000.

Margolis, "Therapy for Condyloma Acuminatum: A Review," *Reviews of Infectious Diseases*, 4 supplement, S829-S836, 1982.

Maron, "Enamel erosion resulting from hydrochloric acid tablets," *JADA*, 127:781-784, 1996.

MayoClinic.com, "Periodontitis," *Mayo Foundation for Medical Education and Research (MFMER)*, http://www.mayoclinic.com/health/periodontitis/DS00369/DSECTION=3, 2006.

McBride et al., "Role of Interbacterial Adherence in Colonization of the Oral Cavities of the Gnotobiotic Rats Infected with *Streptococcus mutans* and Veillonella alcalescens," *Immunity and Infection*, 33(2): 467-472, 1981.

Medicine "http://www.nlm.nih.gov/medlineplus/ency/article/001491.htm" as published Dec. 31, 2009.

Merck Manual Home Edition: Periodontitis, Feb. 2003.

National Cancer Institute: definition of Fruit Acid, obtained from the internet at http://www.cancer.gov/dictionary/?CdrlD=613195 on Aug. 2, 2010.

Novotny et al., "Impact of ascorbic acid on selenium-induced growth inhibition of canine mammary tumor cells in vitro," *J. Nutr. Biochem.*, 4:341-345, 1993.

Office Communication issued in Austrian Patent Application No. A 201/201 I, dated Sep. 6, 2011.

Office Communication issued in U.S. Appl. No. 10/497,504 dated Oct. 27, 2006.

Office Communication issued in U.S. Appl. No. 10/497,504 dated Jan. 3, 2007.

Office Communication issued in U.S. Appl. No. 10/497,504 dated Aug. 17, 2007.

Office Communication issued in U.S. Appl. No. 10/497,504 dated Jul. 16, 2008.

Office Communication issued in U.S. Appl. No. 10/497,504, dated Dec. 8, 2008.

Office Communication issued in U.S. Appl. No. 10/497,504, dated Jul. 31, 2009.

Perry, "Handbook of Inorganic Compounds," Taylor & Francis Group, Second Edition, 2011, 548.

Rotruck, "Discovery of the Role of Selenium in Glutathione Peroxide," Selenium in Biology and Medicine, Eds. Spallholz, Martin, Ganther, AVI Publishing Co., pp. 10-16, 1981.

Rudolf et al., "Selenium activates p53 and p38 pathways and induces caspase-independent cell death in cervical cancer cells", *Cell Biology and Toxicology*, 24(2):123-141, 2007.

Schiffman et al., "Human papillomavirus and cervical cancer" The Lancet, 2007, 370, pp. 890-907.

Socransky, "Relationship of Bacteria to the Etiology of Peridontal Disease," *Journal of Dental Research*, 49(2): 203-222, 1970.

* cited by examiner

SELENIUM-CONTAINING COMPOSITIONS AND USES THEREOF

This application is a divisional of U.S. application Ser. No. 12/913,585, filed Oct. 27, 2010, which is a divisional of 10/497,504, filed Nov. 15, 2004, which is a U.S. National Phase Application under 35 U.S.C. § 371 of PCT Application No. PCT/AT02/00336 filed Dec. 4, 2002, which claims priority to Austrian Application No. 1895/2001 filed Dec. 4, 2001, the entire contents of which applications are incorporated herein by reference.

The invention relates to new uses of selenium-containing aqueous solutions as well as pharmaceutically administrable or food-compatible selenium preparations.

Biochemically, all metabolic processes occurring in organic living beings (plants, animals, humans) in the sense of growth, differentiation and energy processes constitute interplays between reductive and oxidative processes. These "redox processes" are in fact expressions of the electron transmission of biochemical reduction equivalents such as, e.g., NADH+H$^+$ (electron donor) to atmospheric molecular oxygen as an oxidant (electron acceptor). The oxidation of our nutrients (fats, carbohydrates, proteins, oxygen) serves for the permanent maintenance and development of our biological structures. On the other hand, it is exactly our cellular and subcellular structures, the tissues and organs they form, and lastly every organic individual, which in their entirety are composed exactly of those structures (nutrients) which must be continuously supplied from outside for the maintenance and development of living organisms, oxidized for energy recovery, but at the same time also serve the maintenance of functional, anatomical and histological structures. In the end, these biological structures are thus as oxidizable as the nutrients that must be oxidized to maintain our energy of life. In order to prevent the "autooxidation" of biological structures, the organic living organism avails itself of endogenous and exogenous "antioxidants". Endogenous antioxidants include enzymes and enzyme systems such as superoxide dismutase, catalases, peroxidases, cholesterol and reduced glutathione, while exogenous antioxidants constitute, for instance, vitamin A, β-carotene, vitamin E, vitamin C or selenium.

The measure for the "antioxidative capacity", i.e., the readiness to transmit electrons to other atoms and molecules, is quantitatively expressed by what is called the "reduction potential" (standard redox potential). The following Table 1 gives a survey on the standard redox potentials of some endogenous and exogenous antioxidants of organic living beings:

TABLE 1

Standard redox potentials of some antioxidants

| $E_o$ (Volt) | System |
| --- | --- |
| +0.82 | $O_2/H_2O$ |
| +0.366 (basic medium) | selenite |
| +0.300 | tocopherol (vitamin E) |
| +0.100 | ubichinon (coenzyme $Q_{10}$) |
| +0.08 | ascorbic acid |
| +0 (+0.16 to −0.02 V) | flavonoids |
| −0.12 | riboflavin (vitamin $B_2$) |
| −0.22 | cystin/cystein |
| −0.23 | G SH/GSSG |
| −0.29 | thioctic acid (α-lipoic acid) |
| −0.32 | NADH + H$^+$/NAD |
| −0.740 (acidic medium) | selenite |

Antioxidants are, thus, atoms and molecules (for the human organism and, above all, nutrient molecules and enzyme complexes) which react more rapidly with metabolic radicals than biological structures. Consequently, they protect our cell, gene and connective tissue structures by capturing metabolic trigger sparks (radicals, peroxides) before those, for instance, unsaturated fatty acids will attack our biomembranes or sulphur-containing components of vital structural or enzymatic proteins. As is apparent from the above Table, certain elements such as, e.g., selenium will alter their standard redox potential at a change of the pH environment in which these compounds are dissolved.

Selenium is an essential trace element for higher animals and man. It exhibits a protective function for proteins against oxidation caused, for instance, by glutathione peroxidase, which contains the aminoacid selenocystein in its active center. A lack of selenium is associated with rheumatism and grey cataract; the Keshan disease, which occurs in some areas of China, is considered as a selenium deficiency disease. Selenites are able to intensify the effects of vitamin E and are responsible for the detoxication of mercury. A protective action of selenium against carcinogens is also postulated.

On the other hand, higher concentrations of selenium are toxic, the toxicity being attributed to the fact that selenium is able to displace the sulfur contained in proteins. Its excretion, as a rule, takes place in the form of selenate via the kidney and the intestines. Disorders of the human body will be caused if the daily nutrition contains more than 1 μg selenium/g (with a minimum content of 0.02 μg selenium/g being required to prevent deficiency symptoms). Overall, the human body contains about 10 to 15 μg selenium.

Symptoms of intoxication also occur with animals at more than 5 to 10 μg selenium/g contained in animal feed, involving, for instance, the inhibition of growth, loss of hair, softening of corns and hoofs, and loss of feathers with birds. Yet, selenium is also necessary for animals in the breeding of chicks, turkeys and pigs, and to avoid specific diseases of farm animals and, in particular, sheep. Sodium selenite and sodium selenate are therefore required as mixed feed additives or pasture fertilizers, because either the natural selenium content of animal and vegetable feeds is often insufficient or the element is insufficiently released.

U.S. Pat. No. 4,668,515 describes a selenium-containing drink which is mixed with citric acid and ascorbic acid, the solution having to have a pH of 2.75 or more. According to that document, the point is primarily to reach a pH of more than 2.75 by adding citric and ascorbic acids, because—according to the premise of that document—sodium selenite would otherwise be inactivated by acids. Thus, acids are added in order to ensure pH stability. The standard redox potential is affected already when using but one of the selected acids, yet this is not addressed there.

U.S. Pat. No. 4,668,515, furthermore, describes the oral administration of these preparations merely to maintain health and prevent the formation of spontaneous tumors of the mammary gland.

DE 44 37 403 A1 describes antioxidants which, amongst others, contain organically bound selenium. The subject matter of that document is based on the combination of different antioxidative substances which are said to result in significant synergistic effects.

However, the antioxidant combination according to DE 44 37 403 A1 is likewise provided only for internal use (the mixture described in that reference constituting an extremely complex mixture of vitamins and trace elements).

Finally, DE 43 35 441 A1 relates to agents for the prophylaxis of cardiovascular diseases, which contain salicylic acid derivatives as well as a selenium-containing compound. Acetyl-salicylic acid is a pharmacon known to improve the rheological properties of blood.

EP 0 000 670 A1 discloses pharmaceutical formulations that may contain selenites or selenates, yet also ascorbic acid. The combination of selenite (or its respectively present oxidation stage) and ascorbic acid entails undesired redox reactions (selenite being reduced to selenium by ascorbic acid) which would reduce the elevated antioxidative potential of a combination of selenite with acids.

U.S. Pat. No. 5,648,389 refers to dermatological disorders. Those disorders are treated with an agent containing glycolic acid, salicylic acid or lactic acid as well as an absorbable dermatological zinc compound, e.g. zinc selenate, as the essential active component. CN 1 126 042 A, according to its abstract, relates to a hygienic cream rich in γ-sodium linolenate (or linolic acid (according to the title)) and selenium, which cream is comprised of vegetable oil and sodium selenite.

DE 43 20 694 C2 discloses the use of selenium compounds to be externally applied in the case of warts. A combination with acids is neither described nor rendered obvious.

In DE 44 19 783 A1, a hair cure-care shampoo containing organic acids and, amongst others, selenium salts is described.

It was the object of the present invention to provide new uses for selenium-containing preparations and to introduce selenite- or selenate-containing preparations to new food/feed-technological as well as pharmaceutical applications, or enhance their actions on these sectors.

In accordance with the invention, this object is achieved by the use of selenite-containing compounds and pharmaceutically acceptable acids selected from citric acid, acetic acid, malic acid, carbonic acid, sulfuric acid, nitric acid, hydrochloric acid, various fruit acids or mixtures thereof, for the preparation of an agent intended for the topical or buccal application, or mucosal administration, in the prophylaxis or treatment of inflammatory diseases.

It has been shown that it is feasible to provide compositions with elevated antioxidative potentials by the addition of such acids to aqueous solutions of inorganic selenium compounds. Surprisingly, the compositions prepared according to the invention, namely, in particular, solutions, gels, emulsions, suspensions, ointments, etc., will also show therapeutic effects if applied in a manner in which this elevated antioxidative potential is preserved at least for some time. This is the case if, upon application on the therapeutic target site, the increased antioxidative potential is still present and has not been diluted, for instance, by application solutions or body liquids like blood (e.g., at intravenous applications) or by gastric or intestinal contents (at oral applications). Accordingly, the present invention relates to the use of these preparations for external (i.e., topical or buccal) application or the direct application on mucous membranes (mucosal application).

It has been shown that the use according to the invention is suitable for a wide range of clinical pictures, particularly prooxidative ones, wherein it is feasible in many cases to combine the treatment according to the invention, or the agent to be used according to the invention, with other therapeutic measures.

In a preferred manner, a pharmaceutically acceptable carrier, preferably silicon dioxide and, in particular, highly disperse silicon dioxide, is added to the agent to be used according to the invention, which carrier is specially prepared for the respective type of application and hence suitable for topical or buccal or mucosal application in a highly specific manner. Such application-specific additives or pharmaceutically acceptable carriers are sufficiently known to the skilled artisan with regard to the respectively desired form of application, and even the respectively concerned mucosa, and readily transferable to the subject matter of the present invention.

The use according to the invention for the prophylaxis and treatment of inflammatory diseases is preferably applied in the field of dental medicine, for instance in the event of periodontal diseases and, in particular, stomatitis, aphthae or leucoplakia.

It has, furthermore, been shown that the agent according to the invention is excellently suitable for the treatment of mycoses. An efficient treatment of external mycoses has, thus, become feasible according to the invention, whereby infections, particularly those with dermatophytes (skin mycoses), can be treated above all with a topical formulation, whereas for infections with yeast or mold fungi means suitably applied on mucosae can be additionally employed. The agent according to the invention is above all suitable for the treatment of superficial mycoses, yet it is also feasible to treat cutaneous and subcutaneous dermatomycoses in accordance with the invention as long as such mycoses can still be reached by the antioxidative potential inherent in the agent according to the invention, i.e., before any dilution of said potential has occurred.

Mycoses derived from *Cladosporium carrionii, Phialophora compacta, Phialophora dermatitidis, Phialophora pedrosoi, Phialophora verrucosa, Sporothrix schenckii, Cephalosporium* spp., *Madurella grisea, Madurella mycetomi, Petriellidium boydii, Aspergillus fumigatus, Rhizopus oryzae, Blastomyces dermatitidis, Coccidioides immitis, Histoplasma capsulatum* and *Paracoccidioides brasiliensis* are preferably combated in accordance with the invention.

During such treatment, the agent to be used according to the invention is preferably supplemented with an antimycotic. Preferred applications in the treatment of mycoses comprise the skin, genitals, ear as well as oral and nasal mucosae.

The selenium-containing agent to be used according to the invention preferably has a pH of below 7.0, preferably below 5.0, particularly below 4.0, during application. Particularly preferred agents according to the invention have pH values ranging from 6.0 to 2.0 and, in particular, 3.0 to 2.5.

Basically, the nature of the food-compatible or pharmaceutically administrable acid added is not critical. Ascorbic acid may, however, lead to a reduction of the inorganic selenium compound to elementary selenium, which in many cases is unsuitable for ready-to-use preparations. Therefore, acids that do not entail any reduction of inorganic selenium compounds to elementary selenium are preferably employed. Especially citric acid, acetic acid, malic acid, carbonic acid as well as other organic and inorganic acids such as, e.g., sulfuric acid, nitric acid, hydrochloric acid, various fruit acids or mixtures of these acids are, thus, particularly well apt for the present invention.

The composition to be used according to the invention may not only be provided in an aqueous solution. Other preferred forms include ointments, gels or emulsions, which are particularly suitable for the topical, buccal or mucosal administration according to the invention.

It goes without saying that the agent to be used according to the invention may additionally contain auxiliary substances like buffer substances, coloring agents, stabilizers or carrier substances and/or further active components such as, e.g., antibiotics, antiviral agents, antimycotics, analgetics or antiinflammatory agents, said auxiliary substances being also usable in any possible combination. The respective type of auxiliary substance or further active component is a function of the respective use in each individual case. The agent is preferably applied on carrier materials, preferably medical sponges and/or other adsorbing materials and, in particular, wound cones. With weeping diseases, the addition of physically adsorbing auxiliary substances of the type including highly disperse silicates has proved to be particularly advantageous.

Other particularly preferred indications of the agent according to the invention comprise the superficial treatment of tumors, the treatment or prophylaxis of infections with papillomaviruses, particularly in the genital region, the topical, buccal or mucosal prevention or treatment of peroxidic diseases, the topical, buccal or mucosal prevention or treatment or radical diseases, the prevention or treatment of inflammatory processes like periodontitis, sunburn, insect bites and inflammatory burn and wound healing processes.

If desired, the buccal treatment of herpes simplex infections as well as of pigmented spots and also the treatment of "dolor post extractionem" can each be effected, above all, with preparations according to the invention in gel or droplet form.

The invention will be explained in more detail by way of the following examples, to which it is, of course, not limited.

EXAMPLES

Example 1

Preparation of an acidified sodium selenite solution

An acidified sodium selenite solution was prepared to have the following composition (per 100 ml):

| | |
|---|---|
| Sodium selenite pentahydrate | 0.111 g |
| Maltodextrin | 0.5 g |
| Citrus flavor | 0.1 g |
| Citric acid | 0.5 g |
| Food dye | 0.01 g |
| Potassium sorbate | 0.1 g |
| Sodium benzoate | 0.05 g |
| Aqua destillata | 99.29 g |

Example 2

Treatment of herpes simplex infections

Twelve adult patients (seven females, five males) as well as eight children. (four females, four males) suffering from diagnosed stomatitis herpetica/aphtosa were buccally administered five droplets five times a day (children having received a ten-fold-diluted solution) and simultaneously treated externally (five time swabbing per day of the affected sites with the droplets), usually over a period of seven days. Seven out of eight children, in addition to the antioxidative selenium therapy, were prescribed local anaesthetics and/or antibiotics and/or antimycotics and/or analgetic: and antiinflammatory agents, but no additional antiviral therapy.

Nine out of twelve adults were exclusively treated with the strongly antioxidative selenium droplets, one out of twelve patients received an antiviral drug (Aciclovir) besides the droplets. The results are indicated in the following Table 2.

TABLE 2

| Patient No. | Sex | Incidence | Previous treatment | Side effects | Success of therapy |
|---|---|---|---|---|---|
| Herpes Labialis Therapy | | | | | |
| 1 | m | 1 y | local ointment therapy | none | 1 |
| 2 | m | monthly | apy | none | 1 |
| 3 | m | 3-5 y | Aciclovir | none | 1 |
| 4 | f | 3 y | Aciclovir | none | 1 |
| 5 | m | — | Aciclovir | — | 1 |
| 6 | f | 3 y | — | none | 2 |
| 7 | f | monthly | Famvir | none | 1 |
| 8 | f | 3-5 y | Aciclovir | none | 1 |
| 9 | f | 3 y | Aciclovir | none | 1 |
| 10 | f | 3 y | Aciclovir Aciclovir | none | 1 |
| Stomatis Herpetica/Aphtosa Therapy | | | | | |
| 11 | m | — | Xylocain | none | 1 |
| 12 | f | — | — | none | 2 |
| 13 | f | — | — | none | 1 |
| 14 | m | — | — | none | 1 |
| 15 | m | — | — | none | 1 |
| 16 | f | — | — | none | 2 |
| 17 | m | — | — | none | 1 |
| 18 | f | — | — | none | 2 |
| 19 | f | — | — | none | 2 |
| 20 | m | monthly | — | none | 2 | m = male
f = female
1 y = once a year
2 y = twice a year
3 y = three a year
3-5 y = three to five times a year
1 = very good
2 = good
3 = insufficient The examination reports of the examining physician revealed excellent therapeutical successes (disappearance of itching, healing of vesicles) in nineteen out of twenty cases already after three to seven days. Those patients who suffered from herpes recurrences showed marked improvements in the recurrence rates (extension of recurrence-free intervals), or even the complete disappearance of recurrences, after the buccal and external application of the droplets as against an Aciclovir therapy.

Example 3

Treatment of pigmented spots

Pigmented spots (socalled age spots) go back to an increased deposition of radically and peroxidically destroyed protein fatty acid and membrane-fat structures in the subcutaneous tissue, appearing as locally delimited light- to dark-brown discolorations having approximately the sizes of pinheads. Three adult persons (two females, one male) applied the selenium droplets described (by rubbing in five to ten droplets five times a day on the affected sites on the back of the hand) over a period of two months. The application resulted in a noticeable reduction of the number of pigmented spots or a brightening of dark pigmented spots, respectively.

Example 4

Treatment of periodontal diseases

Periodontal diseases rank among the most widespread health problems. The composition according to Example I was, therefore, applied as a spraying solution in the following nine patients:

6 patients suffering from stomatitis
3 patients afflicted by aphthae

The patients received one to two spraying strokes three times a day for about one to two weeks. In all of the nine cases, at least a marked improvement of the clinical picture could be observed after the treatment.

TABLE 3

| Patient No. | Sex | Age group | Diagnosis | Duration of therapy | Success of therapy |
|---|---|---|---|---|---|
| 1 | male | 1974 | gingivostomatitis | 9 days | complete regression; visible improvement |
| 2 | male | 1988 | gingivostomatitis | 13 days | visible improvement |
| 3 | female | 1959 | massive gingivo-stomatitis | 7 days | complete regression; visible improvement |
| 4 | male | 1978 | gingivostomatitis | | substantial improvement |
| 5 | female | 1942 | gingivostomatitis | 4 days | substantial improvement |
| 6 | female | 1932 | stomatitis, Candida infection | 6 days | substantial improvement |
| 7 | male | 1968 | aphthae | 6 days | substantial improvement |
| 8 | female | 1945 | aphthae | 3 days | substantial improvement |
| 9 | male | 1972 | aphthae | 4 days | substantial improvement |

Example 5

In the course of the study, 53 patients were treated for "dolor post extractionem" and observed. The goal of the observation series was the reduction of pain and the improvement of wound healing.

Those 53 patients, 30 females and 23 males, suffering from "dolor post extractionem" were treated with a preparation having the following composition:

| | | | |
|---|---|---|---|
| Sodium selenite pentahydrate | | | 0.11 g |
| Maltodextrin | | | 0.5 g |
| Citrus flavor | | | 0.1 g |
| Citric acid | | | 0.5 g |
| Food dye | | | 0.01 g |
| Potassium sorbate | | | 0.1 g |
| Sodium benzoate | | | 0.05 g |
| Aqua destillata | | | 99.29 g |
| n = 53 | sex: F 30 | | 56.6% |
| | M 23 | | 43.4% |
| n = 53 | age: under 30 | 13 | 24.5% |
| | 31 to 50 | 31 | 58.5% |
| | 51 and up | 9 | 17.0% |

Mode of procedure:

After cleansing of the wound with a 0.9% sodium chloride solution, the inlay impregnated with the above-described solution was placed.

Most the patients were between 20 and 35 years old (Table 4).

Also localization was distributed as follows:

| | |
|---|---|
| upper jaw | 34.5% (19 patients) |
| lower jaw | 65.5% (38 patients) |

At the general medical examination, 30% of all patients (i.e., 16 cases) were diagnosed to have diseases like diabetes mellitus and/or arterial hypertension.

53% of all patients (28 cases) had taken analgetics and antibiotics before they began the selenite treatment.

The evaluation of its action was based on the number of treatments until the attainment of freedom from pain:

TABLE 5

| Number of treatments | Patients n = 53 | in % |
|---|---|---|
| 1 | 26 | 49 |
| 2 | 16 | 30 |
| 3 | 9 | 17 |
| 4 | 1 | 2 |
| 7 | 1 | 2 |

Results: 49% of the patients (26 cases) were free from pain after one treatment, 30% of the patients (16 cases) were free from pain after two treatments. Thus, it can be said that freedom from pain was achieved by one to two treatments in 79% of all patients (42 cases).

The extremely surprising results of the present application observations with the preparations to be used according to the invention have, thus, demonstrated that the application of antioxidants with strong (i.e., low) standard reduction potentials is very effective in the case of wounds and, in particular, inflammatory and/or non-inflammatory painful processes in the dental region.

Example 6

Treatment of papillomatoses

Papillomatoses are cauliflower-like growths which are caused by the socalled papillomavirus. From a histological point of view, papillomas are in most cases benign surface-epithelium tumors which are localized on the oral mucosa, the draining urinary tract, the thigh and lower leg as well as the anal and genital mucosae. A progression by papilloma-virus-induced benign tumors to carcinomas may occur after long papilloma persistences.

Three female patients (aged 6, 39, 53) exhibited perianal papilloma warts (verrucae) and were treated with a preparation having the following composition:

| | |
|---|---|
| Methylparaben PH Eur | 0.61 g |
| Polyparaben PH Eur | 0.33 g |
| Sodium sorbate PH Eur | 1.27 g |
| Purified water PH Eur | 993.48 g |
| Citrus flavor | 1.00 g |
| Peppermint oil | 0.20 g |
| Citric acid | 2.00 g |
| Sodium selenite pentahydrate | 1.11 g |
| Aerosil 200 | 30.00 g |
| | 1,030.00 g |

The silicate-containing selenite solution was applied on the afflicted skin sites at a dosage of 3-5 droplets five times a day. In all three patients, the papilloma warts disappeared within a period of 3 weeks. The treatment was stopped after the disappearance of the warts.

The invention claimed is:

1. A method for treating a sunburn, comprising
obtaining a composition comprising a selenite-containing compound and at least one of citric acid, acetic acid, malic acid, carbonic acid, nitric acid, sulfuric acid, hydrochloric acid and a fruit acid, and
topically administering an effective amount of the composition to a skin site of an individual having the sunburn.

2. The method of claim 1, wherein the composition is an aqueous solution and has a pH of below 7.0.

3. The method of claim 2, wherein the composition has a pH of below 5.0.

4. The method of claim 2, wherein the composition has a pH of from 3.0 to 2.5.

5. The method of claim 1, wherein the composition is an ointment, gel, or emulsion.

6. The method of claim 1, wherein the composition comprises a silicon dioxide.

7. The method of claim 1, wherein the composition is on a carrier material.

8. The method of claim 1, wherein the carrier material is a medical sponge or a wound cone.

9. The method of claim 1, wherein the composition comprises sodium selenite and citric acid.

* * * * *